US006070573A

United States Patent [19]
Howe et al.

[11] Patent Number: 6,070,573
[45] Date of Patent: Jun. 6, 2000

[54] FLEXIBLE VALVE FOR ADMINISTERING CONSTANT FLOW RATES OF MEDICINE FROM A NEBULIZER

[76] Inventors: Harvey James Howe, 8914 Higdon Dr., Vienna, Va. 22182; Craig Jonathan Madden, 1172 Southview Dr., Annapolis, Md. 21401; Richard Raphael Rosenthal, P.O. Box 769, Great Falls, Va. 22066

[21] Appl. No.: 08/825,099

[22] Filed: Mar. 27, 1997

Related U.S. Application Data

[62] Division of application No. 08/110,549, Aug. 23, 1993, Pat. No. 5,655,520.

[51] Int. Cl.$^{7}$ .................................................. A61M 11/00

[52] U.S. Cl. ............................... 128/200.14; 128/200.22; 128/200.23

[58] Field of Search ......................... 128/200.14, 200.18, 128/200.21, 200.23, 203.12, 200.22

[56] References Cited

U.S. PATENT DOCUMENTS

| | | | |
|---|---|---|---|
| 2,788,784 | 3/1957 | Birch et al. . | |
| 3,187,748 | 6/1965 | Mitchell et al. . | |
| 4,106,503 | 8/1978 | Rosenthal et al. . | |
| 4,534,343 | 8/1985 | Nowacki et al. . | |
| 4,796,614 | 1/1989 | Nowacki et al. | 128/200.23 |
| 4,852,561 | 8/1989 | Sperry . | |
| 5,655,520 | 8/1997 | Howe et al. | 128/203.12 |

OTHER PUBLICATIONS

Vernay Duckbill Check Valves Sales Literature (3 Pages).

*Primary Examiner*—Aaron J. Lewis
*Attorney, Agent, or Firm*—Rick Martin

[57] ABSTRACT

A nebulizer is improved by placing a flexible valve in the ambient air inlet tube. Inhalation suction and Venturi effect shut down the flexible valve in proportion to the strength of the inhalation. Thus, the same output flow rate is obtained even with variable strength inhalations. Medications can be properly administered by controlled inhalation flow rates.

6 Claims, 5 Drawing Sheets

FLEXIBLE VALVE FOR ADMINISTERING CONSTANT FLOW RATES OF MEDICINE FROM A NEBULIZER

CROSS REFERENCED PATENTS

U.S. Pat. No. 4,106,503 (1978) to Rosenthal et al. is incorporated herein by reference. This application is a divisional of U.S. application Ser. No. 08/110,549, filed Aug. 23, 1993, issued as U.S. Pat. No. 5,655,520 on Aug. 12, 1997.

FIELD OF INVENTION

The present invention relates to fixed rate flow valves particularly useful in administering constant rates of medicine via inhalation.

BACKGROUND OF THE INVENTION

A nebulizer is commonly used in respiratory therapy and in medical research to dispense an aerosol. Atomization of the aerosol occurs as pressurized air is fed into the bottom of the nebulizer bowl. The patient inhales through an outlet orifice at the top of the nebulizer. This forces the aerosol into the respiratory system. It is customary to regulate the time interval of the pressurized air flow with each breath. Short timed bursts of pressurized air are used to atomize the liquid in the nebulizer. The dosimeter shuts off the air flow at predetermined times after each inhalation. When the pressurized air is shut off, no further atomization of the liquid occurs. Then the patient only breathes ambient air which enters through the ambient air inlet at the top of the nebulizer.

It is well understood that each breath of a patient varies in volume and inspiratory flow rate. The nebulizer has an ambient air entrance at the top to accommodate the patient's requirement for air. In operation when a patient inhales with great force, he could inhale all the atomized aerosol in the nebulizer. There traditionally exists an unregulated direct flow of air from the ambient entrance into the patient through the ambient entrance.

However, during weak inspiratory efforts the patient may inhale the atomized aerosol slowly or alternatively, after a strong inspiratory effort the aerosol may enter the respiratory tract at a higher flow rate. Slow inhalation of the aerosol is generally desired in order to allow the aerosolized drug to penetrate deeper into the respiratory tree.

Patients using the above system cannot self-regulate their own inspiratory flow rates. Therefore, wide ranges of inspiratory flow rates for each breath are to be expected. This can create an inconsistent administration of aerosol to the respiratory tree.

Thus, it is desirable to provide a constant output flow rate of atomized drugs regardless of variations in inhalation pressures. The present invention greatly enhances the reproducibility and constancy of the output flow rate of atomized aerosol from a nebulizer by introducing a variable diameter input valve in the ambient entrance. The diameter of the valve reduces increased suction pressure caused by inhalation.

In operation the variable diameter input valve reduces its orifice size by means of collapsing flexible walls. The pressure inside the nebulizer drops in proportion to the patient's inhalation force. The valve's flexible walls collapse in proportion to the pressure differential between ambient and nebulizer chamber pressures. Thus, during strong inspiratory efforts the valve's flexible walls collapse. A smaller input orifice is formed, thereby causing the flow rate of the ambient intake air to remain constant. It is understood that the flow rate of the ambient intake air is the same as the flow rate of the patient's inhalation. This flow rate is the nebulizer's throughput flow rate. A higher velocity reduced volume of air through a narrow orifice is formed while the nebulizer's throughput flow rate remains constant. In the opposite situation the patient performs a weak inspiratory effort. This results in the valve's flexible walls remaining open. A slower but higher volume of ambient air passes through the wider orifice. Overall within the normal limits of human breathing variations, the nebulizer's throughput flow rate through the valve's flexible walls remains constant. The analogous situation would be for a patient to first suck very hard through a tiny straw for three seconds and getting 1000 droplets of medicine. Next the patient would suck very lightly through a wide straw for three seconds and get 1000 droplets of medicine. The result is that the patient inhales his medication at the same rate regardless of how hard he inhales. When the valve is employed with the dosimeter the nebulizer can be configured such that the inspiratory flow rate and the time interval of inspiration is fixed. This enables the operator to characterize the nebulizer under such conditions such that the output of aerosol is consistent from discharge to discharge. When the nebulizer is calibrated by weighing before and after discharge the exact amount of aerosol administered is determined. Selected amounts of aerosolized drug may then be given by adjusting the concentration of drug in the nebulizer accordingly.

SUMMARY OF THE INVENTION

The main object of the present invention is to economically provide an input regulator valve to a mixing chamber wherein variable pressure outputs do not affect the output flow rate. This enables consistent low inspiratory rates from a nebulizer which favors deeper penetration into the respiratory tree for drug administration of bronchodilators, anti-inflammatory drugs, and such other drugs as may be delivered directly to the lung by aerosolization.

Another object of the present invention is to provide an input regulator valve to a mixing chamber wherein variable pressure outputs generated by applying a vacuum to the mixing chamber do not affect (or effect in a predetermined rate of change) the output flow rate.

Another object of the present invention is to improve a nebulizer to administer constant output rates of medication regardless of inhalation pressure.

Another object of the present invention is to utilize an input regulator valve in an aerosol dispenser to administer constant output rate of medication regardless of inhalation pressure.

Other objects of this invention will appear from the following description and appended claims, reference being had to the accompanying drawings forming a part of this specification wherein like reference characters designate corresponding parts in the several views.

The present invention operates using a pressure differential and the Venturi effect (to a small extent). The Venturi effect simply stated is the faster the flow rate, the slower the pressure inside a pipe. The slower the flow rate, the higher the pressure inside a pipe.

The present invention uses a flexible pipe as a regulating valve. When the flow rate through the regulating valve is low, the pressure differential between the inside of the regulating valve (the nebulizer chamber) and the outside of the outside of the regulating valve (ambient pressure) is minimal. Thus, the flexible walls of the regulating valve remain open.

However, when the patient inhales strongly the pressure differential between the inside of the regulating valve and the outside of the regulating valve is maximal. Thus, the flexible walls of the regulating valve collapse inwards, thereby restricting the flow rate to the patient.

One attractive use for the present invention is in respiratory therapy. A nebulizer generally is constructed as an atomizing chamber having a fluid reservoir on the bottom, a pressurized air input at the bottom to atomize the fluid, a patient output tube at the top, and an ambient air entrance tube also at the top.

In operation, small amounts of pressurized air are input in half second bursts at the bottom of the nebulizer. This atomizes the liquid antigen in the reservoir, thereby forming an aerosol in the nebulizer chamber. The patient inhales from the patient output tube. Exhalations are made away from the nebulizer. The patient's inhalation pressure draws a mixture of aerosol and ambient air into the patient's lungs. The present invention inserts a flow regulating valve in the ambient air entrance tube.

During heavy inhalation, a pressure differential and the Venturi effect causes the flexible walls of the flow regulating valve to collapse. Thus, the patient cannot increase the flow rate of his inhalation regardless of how hard he breathes. During light inhalations, the pressure differential and the Venturi effect become negligible. The resilient, flexible walls of the flow regulating valve remain open. Thus, the patient draws his breath at the same rate as if he breathed hard.

BRIEF DESCRIPTION OF THE DRAWINGS

FIG. 1(*a*) is a side plan view of a nebulizer having a partial cutaway showing the flexible valve.

FIG. 1(*b*) is a close up front plan view of the nebulizer of FIG. 1(*a*).

FIGS. 3(*a*), 3(*b*), 3(c) are front plan views looking into the tapered end of the flexible valve form inside the nebulizer during weak, medium, and strong inhalations, respectively.

FIGS. 6(*a*) and 6(*b*) are diagrams of the flexible valve showing flow direction and the nozzle area.

FIGS. 7(*a*) and 7(*b*) are charts showing the relationship area A to pressure drop.

Before explaining the disclosed embodiment of the present invention in detail, it is to be understood that the invention is not limited in its application to the details of the particular arrangement shown, since the invention is capable of other embodiments. Also, the terminology used herein is for the purpose of description and not of limitation.

DESCRIPTION OF THE PREFERRED EMBODIMENT

Figure 1A:
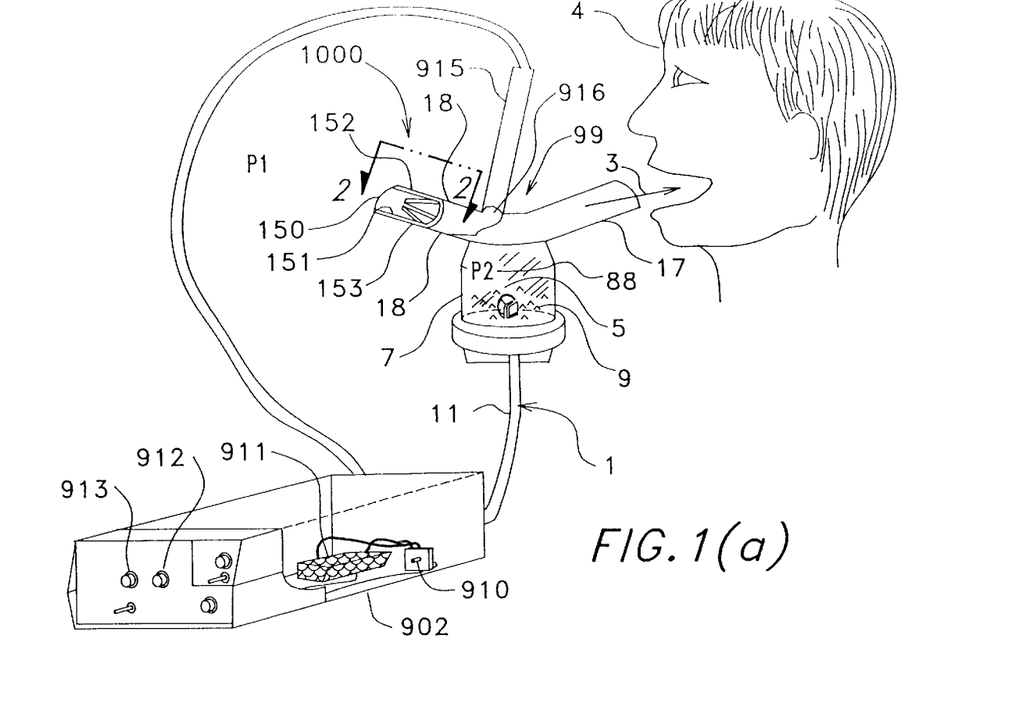

Referring first to FIG. 1(*a*), a nebulizer 99 has a bowl portion 7 which is normally filled with a liquid antigen 9. Pressurized air is fed into tube 11 at entrance 1 via known means of a pressurized tank usually set at 30 p.s.i., and a dosimeter 902 to pulse the air input and prevent excess atomization. See U.S. Pat. No. 4,106,503 (1978) to Rosenthal et al. incorporated herein by reference for a detailed disclosure. The atomizing chamber 88 becomes filled with atomized antigen 5 as the air passes through the liquid antigen 9 in a known manner.

The dosimeter 902 has a pressure sensor 910 which senses the onset of an inhalation. An electronic controller has a duration selector 913 for selecting the length of the air pulse to be delivered to the nebulizer 99 via tube 11. A time delay selector 913 allows the operator to time the pulse with the maximal expansion of the lungs. This maximizes the aerosol penetration into the respiratory tree.

The extension 915 has a one way valve 916. This allows the simultaneous hook-up of the dosimeter 902 to the nebulizer 99. Extension 915 provides vacuum sensing input to the dosimeter 902. This vacuum is caused by the patient's inhalation.

Figure 1B:
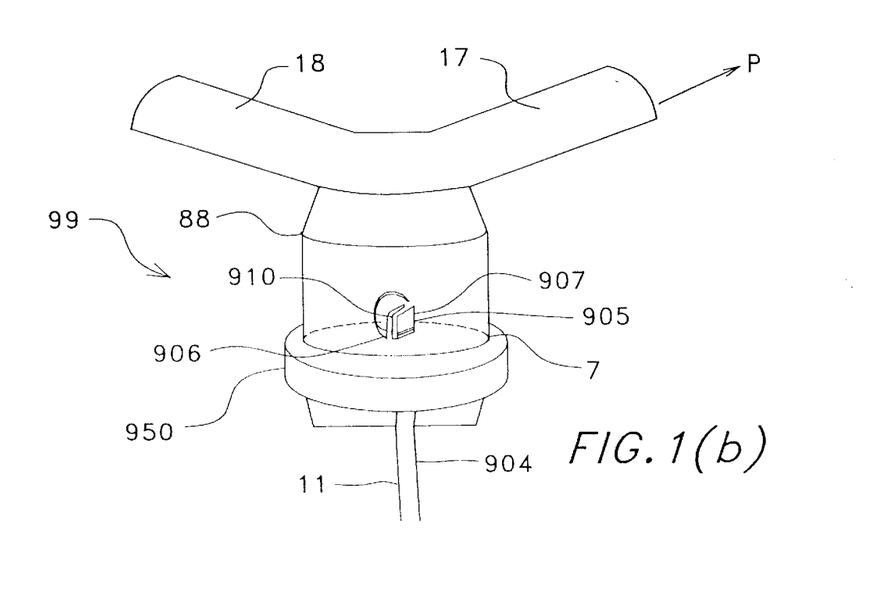

In FIG. 1(*b*) the liquid antigen 9 is in the bowl portion 7 of the bottom half 950 of the nebulizer 99. The tube 11 is connected to an inlet port 904 which ends in an outlet jet 905. Air is blasted against the baffle 907. A straw 906 is immersed in the liquid antigen 9. As the air passes by the outlet 910 of straw 906, the Venturi effect causes a pressure drop. This pressure drop causes liquid antigen 9 to be drawn up the straw 906, into the air stream, and against the baffle 907. The atomization of the liquid antigen 9 occurs in this known manner.

It has been known in the prior art that alignment of the baffle 907 pointing toward the patient's output tube 17 in direction P improves the consistency of the atomization, and consequently improves the repeatability of administering precise quantities of aerosol with each breath. This alignment technique used in combination with flexible valve 1000 permits maximal control of administered aerosol.

The patient 4 inhales through tube 17 in direction 3 thereby inhaling the atomized antigen 5 into his respiratory system. Concurrently during inhalation, the flexible valve 1000 allows a certain amount of ambient air to enter the atomizing chamber 88 via inlet 2 of tube 18.

Figure 2:
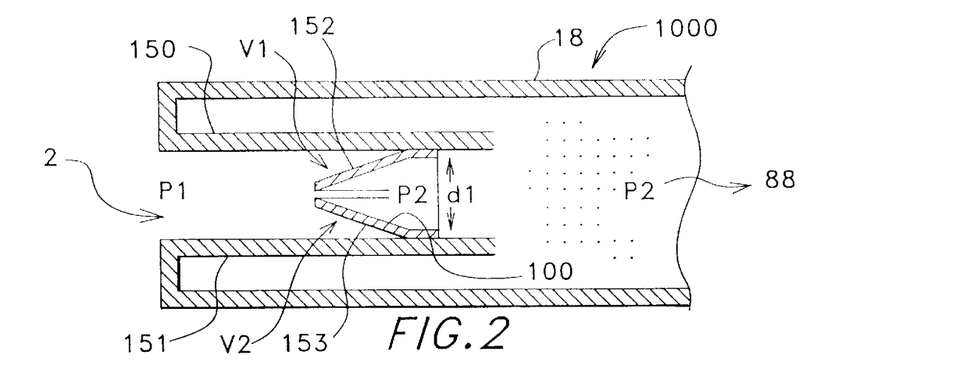
FIG. 2 is a longitudinal cross sectional view of the flexible valve taken along line 2—2 in FIG. 1.

Referring next to FIG. 2, ambient air flows through inlet 2 of tube 18 due to the inhalation pressure drop at $P_2$ which is caused by the patient's inhalation. Ambient air flows into the atomizing chamber 88 between valve lips 152,153. $P_2$ is now lower than $P_1$. This causes force vectors $V_1$, $V_2$ to close valve lips 152, 153. The Venturi effect also adds to vectors V1, V2. Thus, $P_2$ drops due to the patient's inhalation and the Venturi effect.

The lips 152, 153 are flexible. They are preferably made of any flexible resilient material such as rubber, plastic, silicon, neoprene, nitrate, fluorocarbon, vinyl, propylene, butyl, or other compounds. The flexible valve 1000 is constructed to maintain a fixed diameter $d_1$, at flex point 100 during all flow conditions. Only the lips 152, 153 are flexible under pressure drops between $P_1$ and $P_2$. Mounting supports 150, 151 secure the flexible valve 1000 inside tube 18.

Figure 3A:
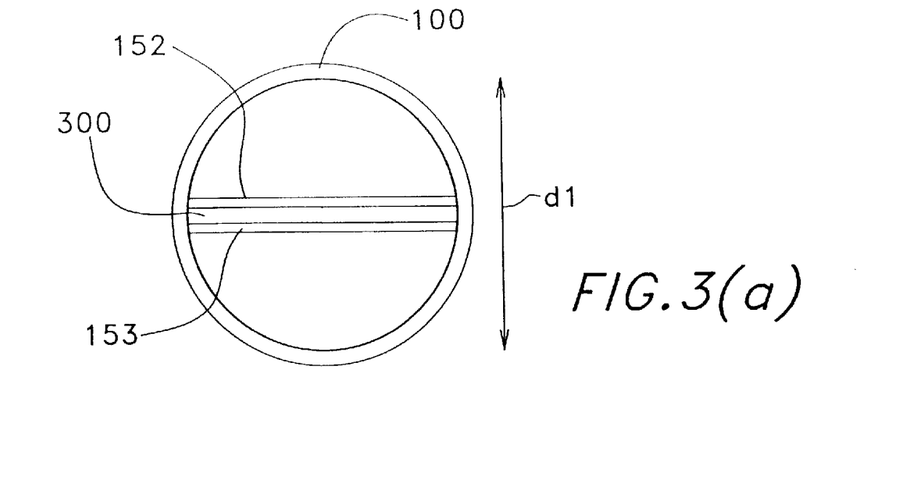
Figure 3B:
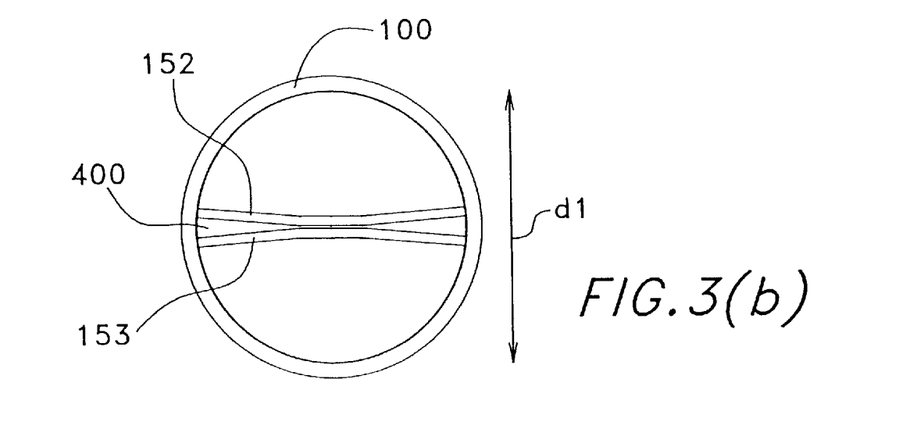

Referring next to FIG. 3(*a*), the patient is inhaling very weakly. Thus, the orifice 300 between lips 152, 153 have been forced together forming a smaller orifice 400. Thus, the output flow has remained constant due to the higher speed air through the smaller orifice 400.

Figure 3C:
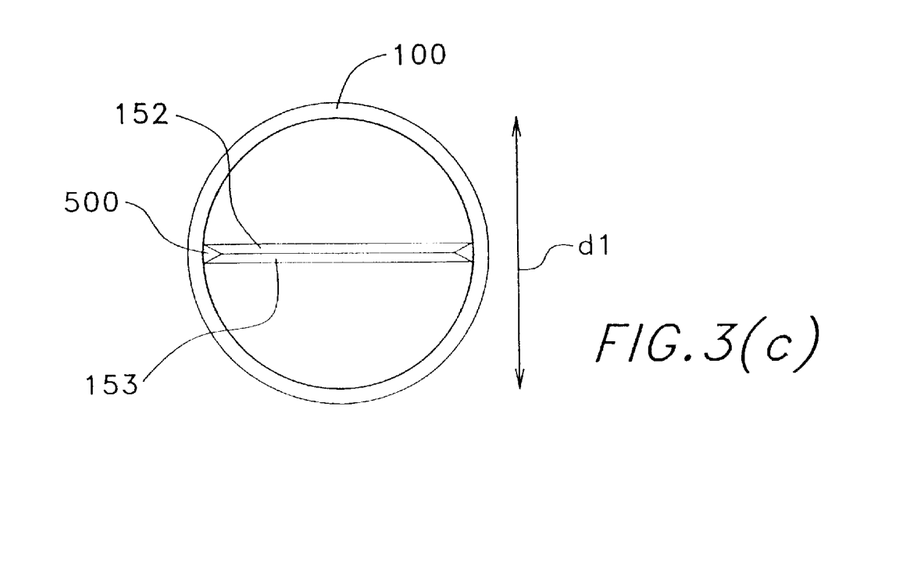

Finally, in FIG. 3(c), the patient has drawn a strong breath. The pressure drop of $P_2$ has practically closed off orifice 500. The output flow rate remains constant. In all instances the ambient air input into the nebulizer is the same as the nebulizer output pulled in by the patient The exact distortion of lips 152, 153 depends on numerous variables including inhalation flow rate, fluid density, and ambient pressure differentials between $P_1$ and $P_2$. Variable flow compensations can be achieved by various types of lips 152, 153, the length to width ratio of the orifice 300, the wall angles and length, as well as the material properties. The nebulizer's output flow rate and orifice closure can be controlled in any desired way for various pressure differences, not necessarily to a constant value. It is, therefore, possible to design the lips 152, 153 in such a manner as to create a customized relationship between the nebulizer's throughput and the patient's inhalation pressure.

EXAMPLE

The effects of regulating the inspiratory flow rate (0.25 L/sec) with a newly created valve and fixation of the nebulizer straw and baffle position were studied as means of enhancing the output reproducibility of the DeVilbis 646 nebulizer when used with a Dosimeter.

Twelve patients took 10 breath actuated inhalations of saline from a nebulizer attached to a Dosimeter set at 0.6 seconds. After disassembly and refill, the 10 breath sequence w repeated 4 more times. All patients conducted this procedure with nebulizers configured as follows: A: Random or varied position of straw and baffle without valve in place; B: Position of straw and baffle fixed without valve in place; C: Straw and baffle fixed with valve in place. The average weights of aerosol (mg) delivered was as follows: A: 0.09634+/−0.002847, B: 0.08057+/−0.002128, C: 0.06691+/−0.000859. All group means were significantly different from one another (p=0.01).

Fixation of the straw and baffle position increased the reproducibility of nebulizer output between nebulizer refills with considerable further enhancement by the addition of a special valve that regulated the inspiratory flow rate. These measures enable the calibration of the DeVilbis 646 nebulizer when a Dosimeter is used, thereby enabling delivery of specific target quantities of aerosol at a known inspiratory flow rate.

Figure 9:
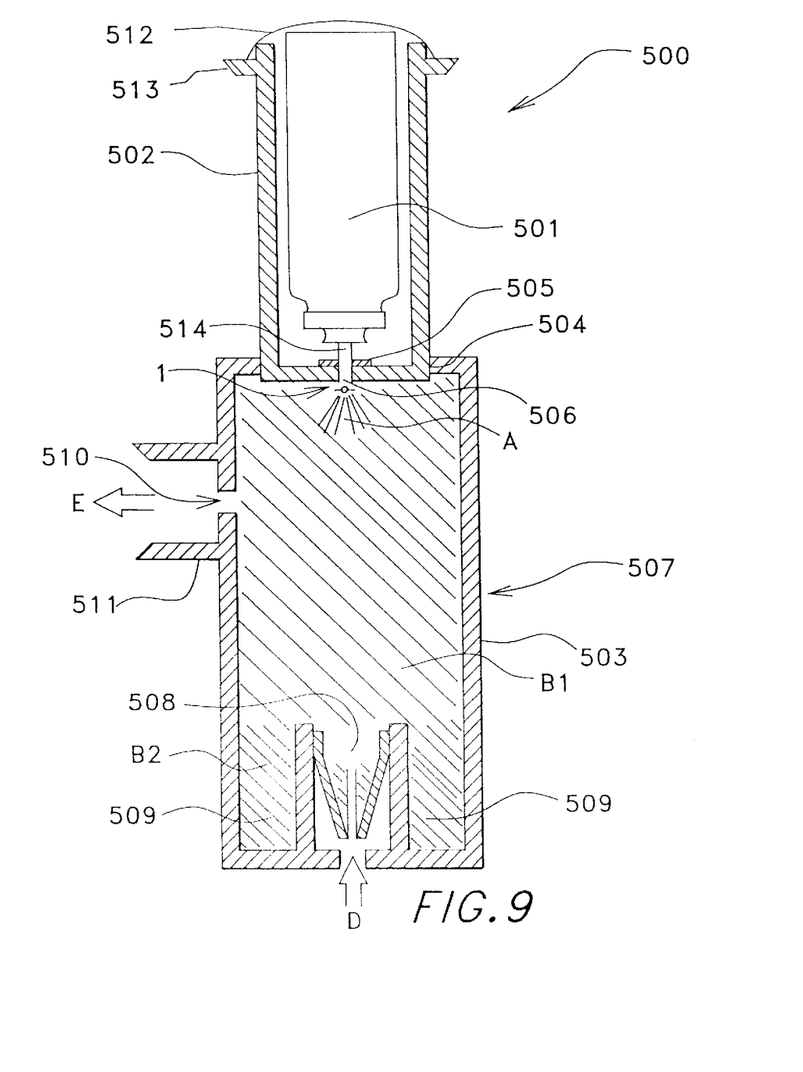
FIG. 9 is a sectional view of the flexible valve in a portable metered dose inhaler.

Referring last to FIG. 9 a drug delivery system (DDS) 500 is shown in sectional view. DDS 500 is a portable, pocket size device used to dispense and inspire medications from a conventional metered dose inhaler (MDI) 501. The primary design features of the DDS 500 are:

Flow rate control of the mixture of inspiratory and medication.

Gravitational and aerodynamic separation of the atomized medication by particle size.

The physical components of the DDS 500 are designated with numbers. The medication, propellants, and air that are not permanent parts of the DDS 500 are designated with letters. A tube body 503 is cylindrical in shape. It houses a conventional MDI 501, a seal retainer 504, a discharge tube seal 505, and a discharge seat 506. The tube body 502 telescopes into the medication separation chamber 507 when not in use. Retainer strap 512 holds the MDI 501 in place.

The MDI 501 can be any number of commercially available atomizing medication dispensers using liquid propellants (preferably fluorocarbons) in a canister. Seal retainer 504 releasably holds the tube body 502 to the medication separation chamber 507. The discharge tube seal 505 is a soft o-ring seal (preferably made of silicon or butyl). It holds and releasably seals the discharge tube 514.

The discharge seat 506 is a notch that restrains the movement of the discharge tube 514 thereby enabling the activation of the MDI 501. The medication separation chamber 507 receives the MDI 501 discharge blasts A. It also houses the tube body 502 when not in use.

The flow control valve 508 is identical to that described as the valve body 1000 of FIGS. 1–8. The large particle well 509 is the bottom portion of the medication separation chamber 507. The large medication particles B2 precipitate therein. Large medication particles B2 thereby keep clear of the inlet air stream D.

The medication chamber exit 510 is an orifice for the mixture of small medication particles B1 and air to exit to the mouthpiece 511. The mouthpiece 511 is a tube from the medication separation chamber 507 to the patient for inspiration of the aerosol medication. The telescoping stop 513 is a circumferential ring that stops the tube body 502 from over-inserting into the medication separation chamber 507. It may also be used as a grip for retraction of tube body 502 to the operational position shown in FIG. 9.

The tube body 502 can be made of molded plastic. The seal/retainer 504, discharge tube seal 505, and flow control valve 508 can be made from the group consisting of rubber, vinyl, plastic, silicon, fluorosilicon, fluorocarbon, nitrile, butyl, or nylon.

In operation the tube body houses members 501, 504, 505 and 506 in their correct working relative positions. The MDI 501 is discharged in the normal way, i.e., by depressing the MDI 501 relative to the discharge tube 514 until the contents of the MDI 501 are released. The metered charge A contains medication, a medication vehicle (usually a fatty acid), and propellants (usually a combination of fluorocarbons). The tube body 502 and the medication separation chamber 507 seal/retainer 504 holds the tube body in their correct operating positions and provides a seal. The discharge tube seal 505 is an o-ring type of seal that does not allow air to enter the chamber during use. The discharge seat 506 is simply a stop that restricts movement of the MDI discharge tube 54 so that the MDI 501 can be pushed into the medication separation chamber 507. This component is common to most MDI dispensers, and is not a significant aspect of this device.

Upon activation of the MDI 501 its discharge A enters the multi-function medication separation chamber 507. This chamber performs the following functions:

1. Cushion the MDI discharge blast A and hold the aerosol medication B1, B2 statically for comfortable patient inhalation not requiring coordination with the MDI activation.
2. Separates the small desirable aerosol medication droplets, B1, from the larger undesirable droplets, B2. The design features that allow these functions to be performed are described below:

(1) MDI Discharge Cushion

The MDI discharge is strong enough to be Undesirable because it is uncomfortable for patients and, due to its high momentum, deposits much of the aerosol medication on the patient's throat and mouth. The medication separation chamber 507 acts as a damper and cushion for the discharged propellant and medication. The very high vapor pressures of the most common fluorocarbon propellants force these propellants to vaporize very rapidly when exposed to ambient conditions. When the MDI charge chamber valve is open, the vapor pressure forces the liquid propellant, vehicle, and medication mixture out of the MDI with considerable velocity. Immediately after jettison, the propellant very rapidly vaporizes breaking the vehicle/medication droplets into smaller and smaller pieces, B1, B2. However, there is still momentum of the mixture away from MDI. The medication separation chamber, 507, has a nearly closed volume, and, thus, slows the momentum of the MDI discharge by the increasing back pressure at the closed end of the chamber. At the end of this process the atomized vehicle/medication droplets B1 are nearly static in the chamber for patient inspiration without the problems of MDI blast and the normally required MDI activation and inhalation coordination.

(2) Separation of Aerosol Droplets by Size

Current literature on MDI efficiency indicates that, of the wide distribution of atomized medication vehicle droplet sizes produced by most MDIs, only droplets of 8 microns or less are inspired deep into the patient's lungs. Larger droplets are too massive to make the turns of the throat and bronchial tree without being centrifugally thrown onto the walls of the respiratory track. Here they are absorbed into the patient's bloodstream which enhancing respiratory function. The medication separation chamber 507 allows the larger droplets to settle to the bottom of the chamber in three different ways to insure that they are not part of the air-medication mixture E inspired by the user. First, at the time of MDI discharge, the largest droplets directly impact the bottom of the chamber even though a blast dampening, as discussed earlier, is provided. Second, the large particles have a settling rate of one cm/s or more (10 times greater than particles of the optimum size) and simply fall on and adhere to the bottom of the chamber before the patient inspiratory effort begins. Finally, the larger droplets continue to fall during inspiration, because their rate of descent is approximately that of the inspired air's D flow rate through the chamber. The flow rate is relatively low because of the flow rate limit imposed by the flow control valve 508.

The flow control valve 508 is a flexible valve that limits the inlet air flow to a desired maximum, independent of patient maximum effort. Minimum flow rate is obviously user controlled. The design of the flow control valve is provided in the description of FIGS. 1–9. Only the integral function of this valve in this device is discussed here. The valve is designed and fabricated to limit the maximum inspiratory flow rate to the patient primarily for optimum distribution of the aerosol in the lung. This flow rate is 0.5 liters per second for adult users. It is well documented in the current literature. The valve and the resulting maximum flow rate may be easily changed to suit individual patient needs, to take best advantage of current MDI performance, or to best reflect current medical belief. The remaining three components are self explanatory from FIG. 9. The air inlet 900 is simply a perforated end cap to the but 199 that allows free entry of air and protects the flow control valve 508. The medication chamber exit 510 can be sized for maximum patient benefit. It must be kept larger than the maximum orifice of the flow control valve 508. The mouthpiece 11 may be used as a cap for the tube body on the MDI end or may be made to fold onto the tube body.

Although the present invention has been described with reference to preferred embodiments, numerous modifications and variations can be made and still the result will come within the scope of the invention. No limitations with respect to the specific embodiments a disclosed herein is intended or should be inferred.

MATHEMATICAL DISCUSSION

Valve Element Restoring Force

Figure 4:
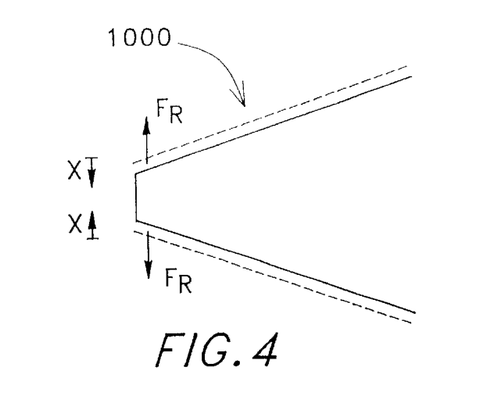
FIG. 4 is a diagram of the flexible valve with dashed lines representing the equilibrium position, and the solid lines representing the compressed position.

If the valve body 1000 in FIG. 4 is deformed then there is a "restoring" force $F_R$ that acts to restore the valve to the original shape. In FIG. 4, the dashed lines represent the equilibrium position of the valve, solid lines represent the compressed position.

The restoring force $F_R$ is proportional to and acts in a direction opposite that of the deflection x.

$$F_R = k_1 x$$

Figure 5:
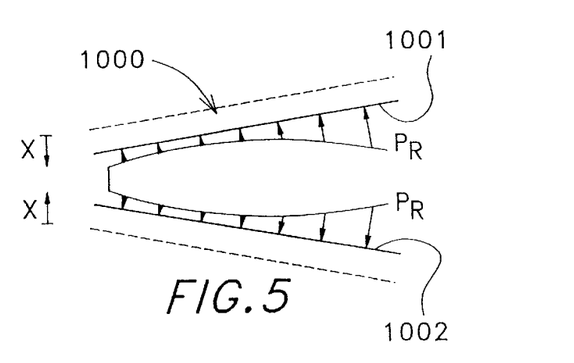
FIG. 5 is a diagram of the restoring pressure $P_R$ acting on the flexible valve.

The valve of the proportionality constant $K_1$ depends on the geometric and material parameters of the valve. $F_R$ is shown above acting on a single pair of points of the valve. However, it would be distributed along the surface as shown in FIG. 5. In general, when a force is distributed over a surface it is referred to as a pressure. The restoring $P_R$ can be variable over the surface. The exact shape of the distribution depends on the geometric and material parameters of the value 1000.

Pressure Driven Flow

Figure 6A:
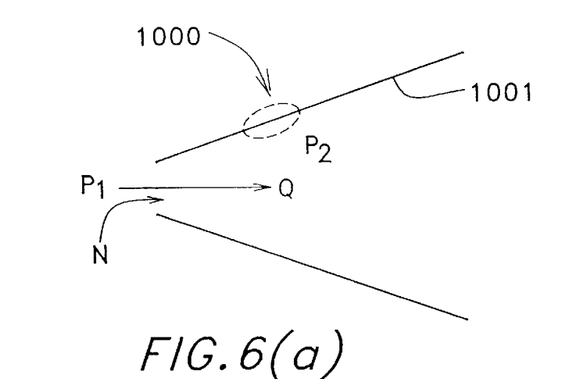

A situation is now analyzed where a pressure drop is imposed across the valve. If a pressure drop is imposed across the valve $P_2 > P_1$ then a flow Q will result. This is shown in FIG. 6(a).

Figure 6B:
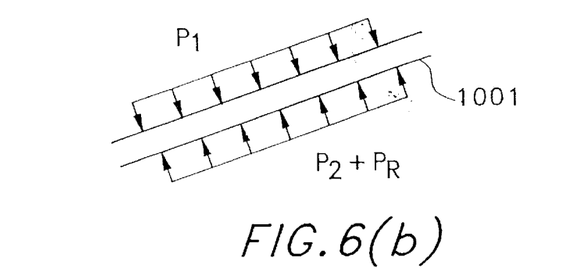

The force balances on the valve surface is shown in FIG. 6 (b). The forces acting on the valve surface must be in equilibrium (because the valve is not in motion). Acting on the inner surface is the pressure $P_2$. Acting on the outer surface is pressure $P_1$. An additional pressure term is required to balance the differences between $P_2$ and $P_1$. This pressure term is the restoring pressure PR (noted above) that accompanies a deformation of the valve. The valve nozzle N (defined as the point of minimum cross section area) will, therefore, decrease in size if $P_2 < P_1$. There will be a slight variation in pressure along the cross section due to the Bernoulli effect (Venturi effect). This variation is slight. The new force balance is shown in FIG. 6(b).

Flow Equation

Figure 7A:
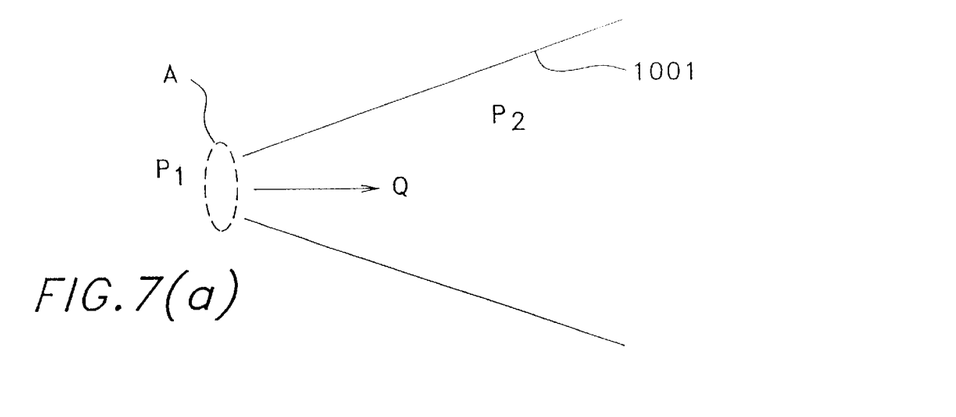
Figure 7B:
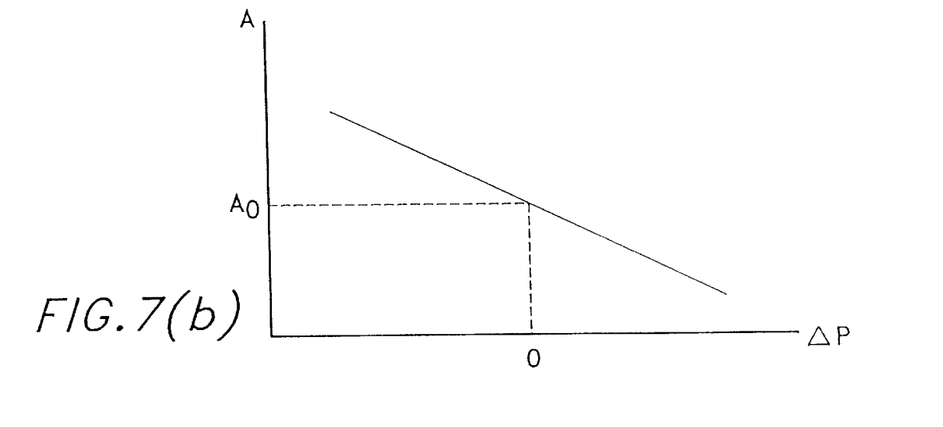

The valve nozzle area A varies depending on pressure drop $\Delta P = P_1 - P_2$. This relationship is shown in FIG. 7(a), 7(b). The shape of the line (or curve) C will depend on the geometric and material parameters of the valve. The important thing to note is that the area A increases with decreasing values of $\Delta P$, and vice versa. The relationship can be expressed mathematically as:

$$A = A_0 - K_2 \Delta P$$

The term $A_0$ is the area corresponding to $\Delta P = 0$. The flow rate Q through the nozzle area A of FIG. 7(a) will depend on the area A and the pressure drop $\Delta P = P_1 - P_2$:

$$Q = K_3 A \sqrt{\Delta P}$$

The flow rate Q is therefore:

$$Q + K_3 A \sqrt{\Delta P} - K_3 K_2 \Delta P$$

The valves of the proportionality constants $K_2$ and $K_3$, depend on the geometric and material properties of the valve. The equation above is plotted in FIG. 8.

Figure 8:
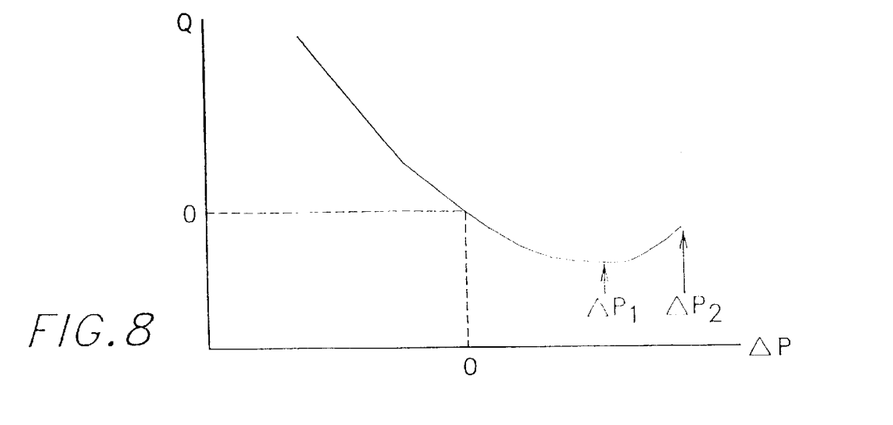
FIG. 8 is a chart showing the relationship of flow rate to pressure drop.

While the shape of the curve will depend on the geometric and material properties of the valve, there are two important things to note:

1. In the nebulizer application shown in FIGS. 1–3 the following is a description of FIG. 8:
    Starting with $\Delta P = 0$ the flow rate Q initially increases with increasing values of $\Delta P$. Increasing $\Delta P$ beyond $\Delta P_1$, is accompanied by a decrease in the flow rate Q. At a high enough value of $\Delta P(\Delta P_2)$ the flow rate will be zero.
2. For other applications $\Delta P < 0$ ($P_2 > P_1$):
    Starts with $\Delta P = 0$ the flow rate in the opposite direction of Q will increase "rapidly" with increasing values of $\Delta P$. This rate of change is much larger than observed with the area because of the $\Delta P$ term is the flow equation.

The valve must be configured such that P1 is atmospheric and P2 is the pressure within the nebulizer chamber. When the patient breathes the observed condition is $P_2, P_1$ ($\Delta P$,0). If the magnitude of $\Delta P$ exceeds $\Delta P_1$, then the amount of air entering the nebulizer through the valve decreases.

It is understood that the placement of the above described valve in a nebulizer could be either in the inlet or the outlet portion thereof. It is further understood that the above described valve also functions as a safety valve for pressure release should an accidental pressurization occur in the nebulizer.

Although the present invention has been described with reference to preferred embodiments, numerous modifications and variations can be made and still the result will come within the scope of the invention. No limitation with respect to the specific embodiments disclosed herein is intended or should be inferred.

I claim:

1. A portable drug delivery system comprising:

a tube body;

a medication separation chamber;

a connection between the tube body and the medication separation chamber;

said tube body further comprising a pressurized metered dose inhaler for injecting a metered blast of medication from the pressurized metered dose inhaler into the medication separation chamber;

said medication separation chamber further comprising a patient inhalation mouthpiece having an exit orifice from the medication separation chamber;

a patient initiated variable vacuum on the mouthpiece creating an output flow; and said medication separation chamber further comprising an air inlet orifice having a flexible valve with a variable cross-sectional orifice resulting in a constant output flow rate of the metered blast of medication regardless of the patient initiated variable vacuum other than for a zero vacuum.

2. The drug delivery system of claim 1, wherein said medication separation chamber further comprises a bottom portion for collecting large drops of the metered blast of medication.

3. The drug delivery system of claim 1, wherein said flexible valve further comprises a flexible nozzle having a set of flexible lips angled toward one another forming the cross-sectional orifice facing upstream of airflow, said patient initiated vacuum reducing a cross-sectional area of the orifice by collapsing the flexible lips in proportion to the increased vacuum.

4. A portable drug delivery system comprising:

a tube body connected to a medication separation chamber;

a union between the tube body and said medication separation chamber;

said tube body further comprising a pressurized metered dose inhaler having an injector for injecting a metered blast of medication from the pressurized metered dose inhaler into the medication separation chamber;

said medication separation chamber further comprising a patient inhalation mouthpiece having an exit orifice from the medication separation chamber;

said medication separation chamber further comprising an air inlet orifice having a flexible valve;

a patient initiated variable vacuum on the mouthpiece creating an output flow from the medication chamber;

said flexible valve having a nozzle which varies in its cross-sectional area; and said nozzle having flexible walls forming an orifice and having an exposure upstream to ambient pressure and exposure downstream to a medication separation chamber pressure, wherein said patient initiated variable vacuum reduces a cross-sectional area of the orifice by collapsing the flexible walls in proportion to an increased vacuum, resulting in a constant output flow rate of the medication regardless of the patient initiated variable vacuum other than for a zero vacuum.

5. The drug deliver system of claim 4, wherein said medication separation chamber further comprises a bottom portion for collecting large drops of the metered blast of medication.

6. The drug delivery system of claim 4, wherein said flexible walls further comprise a material selected from the group consisting of rubber, plastic, silicon, neoprene, nitrate, fluorocarbon, vinyl, propylene, and butyl.

* * * * *